United States Patent [19]

Dawson et al.

[11] Patent Number: 4,526,787

[45] Date of Patent: Jul. 2, 1985

[54] N-HETEROCYCLIC RETINOIC ACID ANALOGUES

[75] Inventors: Marcia I. Dawson, Menlo Park; Rebecca L. S. Chan, Palo Alto; Peter D. Hobbs, Redwood City, all of Calif.

[73] Assignee: SRI International, Menlo Park, Calif.

[21] Appl. No.: 479,182

[22] Filed: Mar. 28, 1983

[51] Int. Cl.³ .................. C07D 213/79; C07D 239/54; A61K 31/505; A61K 31/455

[52] U.S. Cl. .................... 514/255; 544/335; 544/406; 546/323; 546/326; 548/343; 514/256; 514/354; 514/400; 514/861

[58] Field of Search ............... 544/335, 406; 546/326, 546/323; 548/343; 424/250, 251, 266, 273 R

[56] References Cited

FOREIGN PATENT DOCUMENTS 2440525  6/1975  Fed. Rep. of Germany .

OTHER PUBLICATIONS

Boutwell, R. K., et al., "Advances in Enzyme Regulation" vol. 17, ed. Weber, G. Pergamon Press, (1979).
Verma, A. K., et al., "Cancer Res." (1979), 39:419–427.
Dawson, M. I., et al., J. Med. Chem., (1981) 24:583–592, 1214–1223.

Primary Examiner—Henry R. Jiles
Assistant Examiner—Dale A. Bjorkman
Attorney, Agent, or Firm—Ciotti & Murashige

[57] ABSTRACT

A compound of the formula:

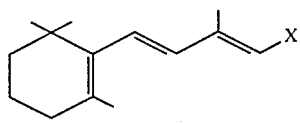

where X is

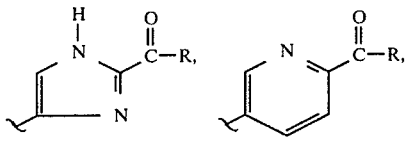

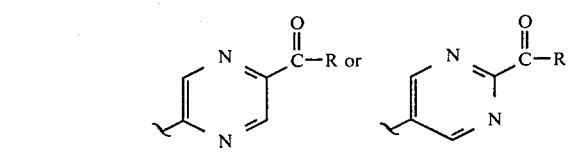

and R is hydroxy, or an alkoxy with 0 or 1 hydroxy substituent, or aroxy with 0 or 1 hydroxy substituent, or alkoxy monosubstituted phenoxy, or $NR^1R^2$ where $R^1$ is hydrogen, or an alkyl or aryl with 0 or 1 hydroxy substituent, and $R^2$ is an alkyl or aryl with 0 or 1 hydroxy substituent. These compounds are useful as chemopreventive agents for inhibiting tumor promotion in epithelial cells and for treating nonmalignant skin disorders.

18 Claims, No Drawings

N-HETEROCYCLIC RETINOIC ACID ANALOGUES

REFERENCE TO GOVERNMENT GRANT OR CONTRACT

The invention described herein was made in the course of work under grant from the National Institutes of Health.

DESCRIPTION

1. Technical Field

The invention is in the fields of retinoid chemistry and chemotherapy. More particularly, the invention relates to certain N-heterocyclic retinoic acid analogues.

2. Background Art

The progressive loss of the regulation of cellular differentiation by epithelial cells can result in cancer. Retinoic acid and some of its analogues (retinoids) have been investigated as "chemopreventive" agents, that is, agents that interfere with tumor promotion in epithelial cells. Boutwell, R. K., et al, *Advances in Enzyme Regulation* V.17, Ed. Weber, G., Pergamon Press (1979); Verma, A. K., et al, *Cancer Res* (1979) 39:419–427; Dawson, M. I., et al, *J Med Chem* (1980) 23:1013–1022 and *J Med Chem* (1981) 24:583–592.

The latter Dawson, M. I., et al, article reports the preparation of (1E,3E)-and (1Z,3E)-1-(4-carboxyphenyl)-2-methyl-4-(2,6,6-trimethyl-1-cyclohexen-1-yl)-1,3-butadiene, the methyl and ethyl esters thereof, (E)-1-(2-carboxyphenyl)-4-methyl-6-(2,6,6-trimethyl-1-cyclohexen-1-yl)-1,3,5-hexatriene and the methyl ester thereof, (E)-1-[2-(tetrahydropyranyloxy)phenyl]-4-methyl-6-(2,6,6-trimethyl-1-cyclohexen-1-yl)-1,3,5-hexatriene and the (1E,3Z,5E) isomer thereof, and (E)-1-(2-hydroxyphenyl)-4-methyl-6-(2,6,6-trimethyl-1-cyclohexen-1-yl)-1,3,5-hexatriene and its (1E,3Z,5E) isomer. Some of these aromatic retinoic acid analogues exhibited biological activity in the ornithine decarboxylase (ODC) assay, which assay is described by Verma, A. K. and Boutwell, R. K., *Cancer Res* (1977) 37:2196–2201.

A principal object of this invention is to provide N-heterocyclic retinoic acid analogues which are biologically active and which may exhibit lesser toxicity than other aromatic retinoic acid analogues.

DISCLOSURE OF THE INVENTION

The heterocyclic retinoic acid analogues of the invention are compounds of the formula:

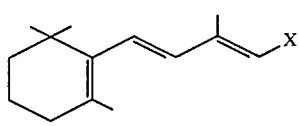

(1)

In formula (1), X may be any one of the following 5 or 6 annular atom N-heterocyclic groups:

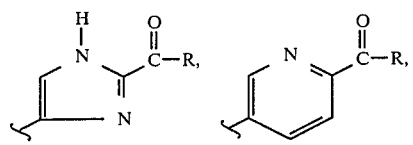

-continued

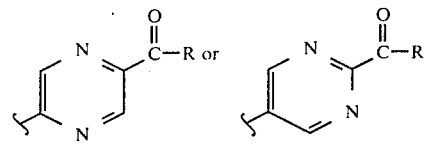

where R is hydroxy, alkoxy with 0 or 1 hydroxy substituent, aroxy, or $NR^1R^2$ where $R^1$ is hydrogen, alkyl with 0 or 1 hydroxy substituent, or aryl and $R^2$ is alkyl with 0 or 1 hydroxy substituent or aryl.

When used as pharmaceuticals, eg, as a chemopreventive agent or for treating skin disorders such as proliferative skin diseases or acne, one or more of these retinoids is combined with a suitable pharmaceutically acceptable carrier and an effective dose thereof is administered to the patient.

MODES FOR CARRYING OUT THE INVENTION

The alkoxy groups represented by R will usually contain 1 to about 10 carbon atoms and have 0 or 1 hydroxy substituents, preferably 1 to 4 carbon atoms, and have 0 or 1 hydroxy substituent and the aroxy groups represented thereby will usually be mononuclear and contain 6 to 15 carbon atoms, more usually 6 to 10 carbon atoms and have 0 or 1 hydroxy substituent. Preferred aroxy groups are phenoxy and hydroxy- or $C_1$-$C_4$ alkoxy-monosubstituted phenoxy. The alkoxy groups represented by R may be straight chain or branched chain. Examples of such alkoxy groups are methoxy, ethoxy, n-propoxy, i-propoxy, n-butoxy, s-butoxy, t-butoxy, n-pentoxy, n-hexoxy, 2-methylpentoxy, n-heptoxy, 2-hydroxyethoxy, 3-methylhexoxy, n-octoxy, and n-decoxy. Examples of aroxy groups are phenoxy, o-, m-, p-hydroxyphenoxy, o-, m-, p-methoxyphenoxy, toloxy, cumoxy, xyloxy, and naphthoxy.

The alkyl groups represented by $R^1$ and $R^2$ may be straight chain or branched chain. They will typically each contain 1 to 8 carbon atoms with 0 or 1 hydroxy substituent, preferably 1 to 4 carbon atoms, and have 0 or 1 hydroxy substituent. Examples of such alkyl groups are methyl, ethyl, propyl, isopropyl, n-butyl, s-butyl, n-amyl, n-hexyl, 2-methylamyl, n-heptyl, 3-methylhexyl, n-octyl, hydroxymethyl, 2-hydroxyethyl, 3-hydroxypropyl, 2-hydroxyhexyl, and the like. The corresponding aryl groups represented by $R^1$ and $R^2$ may be substituted or unsubstituted mononuclear or polynuclear moieties. The substituents will usually be lower (ie, 1 to 4 carbon atoms) alkyl, monohydroxyalkyl, lower alkoxy, monohydroxyalkoxy or hydroxy. When substituted, the group will usually be mono-substituted. Examples of such groups are phenyl, o-, m-, or p-hydroxyphenyl, o-, m-, or p-methoxyphenyl, ethylbenzyl, cumyl, and the like. These aryl groups will usually contain 6 to about 15 carbon atoms, more usually 6 to 10 carbon atoms. Phenyl, 4-hydroxyphenyl, and 4-methoxyphenyl are preferred aryl groups.

Examples of acids (R=OH) represented by formula (1) are:

(E)-1-(2-carboxy-4-imidazolyl)-2-methyl-4-(2,6,6-trimethyl-1-cyclohexen-1-yl)-1,3-butadiene.

(E)-1-(2-carboxy-5-pyridyl)-2-methyl-4-(2,6,6-trimethyl-1-cyclohexen-1-yl)-1,3-butadiene.

(E)-1-(2-carboxy-5-pyrazinyl)-2-methyl-4-(2,6,6-trimethyl-1-cyclohexen-1-yl)-1,3-butadiene.

(E)-1-(2-carboxy-5-pyrimidinyl)-2-methyl-4-(2,6,6-trimethyl-1-cyclohexen-1-yl)-1,3-butadiene.

Examples of esters (R=alkoxy, aroxy) represented by formula (1) are:

(E)-1-(2-carbomethoxy-4-imidazolyl)-2-methyl-4-(2,6,6-trimethyl-1-cyclohexen-1-yl)-1,3-butadiene.

(E)-1-(2-carbethoxy-4-imidazolyl)-2-methyl-4-(2,6,6-trimethyl-1-cyclohexen-1-yl)-1,3-butadiene.

(E)-1-(2-carbisopropoxy-4-imidazolyl)-2-methyl-4-(2,6,6-trimethyl-1-cyclohexen-1-yl)-1,3-butadiene.

(E)-1-(2-carbopropoxy-4-imidazolyl)-2-methyl-4-(2,6,6-trimethyl-1-cyclohexen-1-yl)-1,3-butadiene.

(E)-1-(2-carbobutoxy-4-imidazolyl)-2-methyl-4-(2,6,6-trimethyl-1-cyclohexen-1-yl)-1,3-butadiene.

(E)-1-(2-carbopentoxy-4-imidazolyl)-2-methyl-4-(2,6,6-trimethyl-1-cyclohexen-1-yl)-1,3-butadiene.

(E)-1-(2-carbohexoxy-4-imidazolyl)-2-methyl-4-(2,6,6-trimethyl-1-cyclohexen-1-yl)-1,3-butadiene.

(E)-1-(2-carboheptoxy-4-imidazolyl)-2-methyl-4-(2,6,6-trimethyl-1-cyclohexen-1-yl)-1,3-butadiene.

(E)-1-(2-carboctoxy-4-imidazolyl)-2-methyl-4-(2,6,6-trimethyl-1-cyclohexen-1-yl)-1,3-butadiene.

(E)-1-(2-carbononoxy-4-imidazolyl)-2-methyl-4-(2,6,6-trimethyl-1-cyclohexen-1-yl)-1,3-butadiene.

(E)-1-(2-carbodecoxy-4-imidazolyl)-2-methyl-4-(2,6,6-trimethyl-1-cyclohexen-1-yl)-1,3-butadiene.

(E)-1-[2-carbo-(2-hydroxy)ethoxy-4-imidazolyl]-2-methyl-4-(2,6,6-trimethyl-1-cyclohexen-1-yl)-1,3-butadiene.

(E)-1-[2-carbo-(3-hydroxy)propoxy-4-imidazolyl]-2-methyl-4-(2,6,6-trimethyl-1-cyclohexen-1-yl)-1,3-butadiene.

(E)-1-(2-carbophenoxy-4-imidazolyl)-2-methyl-4-(2,6,6-trimethyl-1-cyclohexen-1-yl)-1,3-butadiene.

(E)-1-(2-carbo-p-hydroxyphenoxy-4-imidazolyl)-2-methyl-4-(2,6,6-trimethyl-1-cyclohexen-1-yl)-1,3-butadiene.

(E)-1-(2-carbo-o-hydroxyphenoxy-4-imidazolyl)-2-methyl-4-(2,6,6-trimethyl-1-cyclohexen-1-yl)-1,3-butadiene.

(E)-1-(2-carbo-p-methoxyphenoxy-4-imidazolyl)-2-methyl-4-(2,6,6-trimethyl-1-cyclohexen-1-yl)-1,3-butadiene.

(E)-1-(2-carbo-p-isopropoxyphenoxy-4-imidazolyl)-2-methyl-4-(2,6,6-trimethyl-1-cyclohexen-1-yl)-1,3-butadiene.

(E)-1-(2-carbo-p-toluoxy-4-imidazolyl)-2-methyl-4-(2,6,6-trimethyl-1-cyclohexen-1-yl)-1,3-butadiene.

(E)-1-(2-carbo-2-naphthoxy-4-imidazolyl)-2-methyl-4-(2,6,6-trimethyl-1-cyclohexen-1-yl)-1,3-butadiene.

(E)-1-(2-carbomethoxy-5-pyridyl)-2-methyl-4-(2,6,6-trimethyl-1-cyclohexen-1-yl)-1,3-butadiene.

(E)-1-(2-carbethoxy-5-pyridyl)-2-methyl-4-(2,6,6-trimethyl-1-cyclohexen-1-yl)-1,3-butadiene.

(E)-1-(2-carbisopropoxy-5-pyridyl)-2-methyl-4-(2,6,6-trimethyl-1-cyclohexen-1-yl)-1,3-butadiene.

(E)-1-(2-carbopropoxy-5-pyridyl)-2-methyl-4-(2,6,6-trimethyl-1-cyclohexen-1-yl)-1,3-butadiene.

(E)-1-(2-carbobutoxy-5-pyridyl)-2-methyl-4-(2,6,6-trimethyl-1-cyclohexen-1-yl)-1,3-butadiene.

(E)-1-(2-carbopentoxy-5-pyridyl)-2-methyl-4-(2,6,6-trimethyl-1-cyclohexen-1-yl)-1,3-butadiene.

(E)-1-(2-carbohexoxy-5-pyridyl)-2-methyl-4-(2,6,6-trimethyl-1-cyclohexen-1-yl)-1,3-butadiene.

(E)-1-(2-carboheptoxy-5-pyridyl)-2-methyl-4-(2,6,6-trimethyl-1-cyclohexen-1-yl)-1,3-butadiene.

(E)-1-(2-carboctoxy-5-pyridyl)-2-methyl-4-(2,6,6-trimethyl-1-cyclohexen-1-yl)-1,3-butadiene.

(E)-1-(2-carbononoxy-5-pyridyl)-2-methyl-4-(2,6,6-trimethyl-1-cyclohexen-1-yl)-1,3-butadiene.

(E)-1-(2-carbodecoxy-5-pyridyl)-2-methyl-4-(2,6,6-trimethyl-1-cyclohexen-1-yl)-1,3-butadiene.

(E)-1-[2-carbo-(2-hydroxy)ethoxy-5-pyridyl]-2-methyl-4-(2,6,6-trimethyl-1-cyclohexen-1-yl)-1,3-butadiene.

(E)-1-[2-carbo-(3-hydroxy)propoxy-5-pyridyl]-2-methyl-4-(2,6,6-trimethyl-1-cyclohexen-1-yl)-1,3-butadiene.

(E)-1-(2-carbophenoxy-5-pyridyl)-2-methyl-4-(2,6,6-trimethyl-1-cyclohexen-1-yl)-1,3-butadiene.

(E)-1-(2-carbo-p-hydroxyphenoxy-5-pyridyl)-2-methyl-4-(2,6,6-trimethyl-1-cyclohexen-1-yl)-1,3-butadiene.

(E)-1-(2-carbo-o-hydroxyphenoxy-5-pyridyl)-2-methyl-4-(2,6,6-trimethyl-1-cyclohexen-1-yl)-1,3-butadiene.

(E)-1-(2-carbo-p-methoxyphenoxy-5-pyridyl)-2-methyl-4-(2,6,6-trimethyl-1-cyclohexen-1-yl)-1,3-butadiene.

(E)-1-(2carbo-p-isopropoxyphenoxy-5-pyridyl)-2-methyl-4-(2,2,6-trimethyl-1-cyclohexen-1-yl)-1,3-butadiene.

(E)-1-(2-carbo-p-toluoxy-5-pyridyl)-2-methyl-4-(2,6,6-trimethyl-1-cyclohexen-1-yl)-1,3-butadiene.

(E)-1-(2-carbo-2-naphthoxy-5-pyridyl)-2-methyl-4-(2,6,6-trimethyl-1-cyclohexen-1-yl)-1,3-butadiene.

(E)-1-(2-carbomethoxy-5-pyrazinyl)-2-methyl-4-(2,6,6-trimethyl-1-cyclohexen-1-yl)-1,3-butadiene.

(E)-1-(2-carbethoxy-5-pyrazinyl)-2-methyl-4-(2,6,6-trimethyl-1-cyclohexen-1-yl)-1,3-butadiene.

(E)-1-(2-carbisopropoxy-5-pyrazinyl)-2-methyl-4-(2,6,6-trimethyl-1-cyclohexen-1-yl)-1,3-butadiene.

(E)-1-(2-carbopropoxy-5-pyrazinyl)-2-methyl-4-(2,6,6-trimethyl-1-cyclohexen-1-yl)-1,3-butadiene.

(E)-1-(2-carbobutoxy-5-pyrazinyl)-2-methyl-4-(2,6,6-trimethyl-1-cyclohexen-1-yl)-1,3-butadiene.

(E)-1-(2-carbopentoxy-5-pyrazinyl)-2-methyl-4-(2,6,6-trimethyl-1-cyclohexen-1-yl)-1,3-butadiene.

(E)-1-(2-carbohexoxy-5-pyrazinyl)-2-methyl-4-(2,6,6-trimethyl-1-cyclohexen-1-yl)-1,3-butadiene.

(E)-1-(2-carboheptoxy-5-pyrazinyl)-2-methyl-4-(2,6,6-trimethyl-1-cyclohexen-1-yl)-1,3-butadiene.

(E)-1-(2-carboctoxy-5-pyrazinyl)-2-methyl-4-(2,6,6-trimethyl-1-cyclohexen-1-yl)-1,3-butadiene.

(E)-1-(2-carbononoxy-5-pyrazinyl)-2-methyl-4-(2,6,6-trimethyl-1-cyclohexen-1-yl)-1,3-butadiene.

(E)-1-(2-carbodecoxy-5-pyrazinyl)-2-methyl-4-(2,6,6-trimethyl-1-cyclohexen-1-yl)-1,3-butadiene.

(E)-1-[2-carbo-(2-hydroxy)ethoxy-5-pyrazinyl]-2-methyl-4-(2,6,6-trimethyl-1-cyclohexen-1-yl)-1,3-butadiene.

(E)-1-[2-carbo-(3-hydroxy)propoxy-5-pyrazinyl]-2-methyl-4-(2,6,6-trimethyl-1-cyclohexen-1-yl)-1,3-butadiene.

(E)-1-(2-carbophenoxy-5-pyrazinyl)-2-methyl-4-(2,6,6-trimethyl-1-cyclohexen-1-yl)-1,3-butadiene.

(E)-1-(2-carbo-p-hydroxyphenoxy-5-pyrazinyl)-2-methyl-4-(2,6,6-trimethyl-1-cyclohexen-1-yl)-1,3-butadiene.

(E)-1-(2-carbo-o-hydroxyphenoxy-5-pyrazinyl)-2-methyl-4-(2,6,6-trimethyl-1-cyclohexen-1-yl)-1,3-butadiene.

(E)-1-(2-carbo-p-methoxyphenoxy-5-pyrazinyl)-2-methyl-4-(2,6,6-trimethyl-1-cyclohexen-1-yl)-1,3-butadiene.

(E)-1-(2-carbo-p-isopropoxyphenoxy-5-pyrazinyl)-2-methyl-4-(2,6,6-trimethyl-1-cyclohexen-1-yl)-1,3-butadiene.
(E)-1-(2-carbo-p-toluoxy-5-pyrazinyl)-2-methyl-4-(2,6,6-trimethyl-1-cyclohexen-1-yl)-1,3-butadiene.
(E)-1-(2-carbo-2-naphthoxy-5-pyrazinyl)-2-methyl-4-(2,6,6-trimethyl-1-cyclohexen-1-yl)-1,3-butadiene.
(E)-1-(2-carbomethoxy-5-pyrimidinyl)-2-methyl-4-(2,6,6-trimethyl-1-cyclohexen-1-yl)-1,3-butadiene.
(E)-1-(2-carbethoxy-5-pyrimidinyl)-2-methyl-4-(2,6,6-trimethyl-1-cyclohexen-1-yl)-1,3-butadiene.
(E)-1-(2-carbisopropoxy-5-pyrimidinyl)-2-methyl-4-(2,6,6-trimethyl-1-cyclohexen-1-yl)-1,3-butadiene.
(E)-1-(2-carbopropoxy-5-pyrimidinyl)-2-methyl-4-(2,6,6-trimethyl-1-cyclohexen-1-yl)-1,3-butadiene.
(E)-1-(2-carbobutoxy-5-pyrimidinyl)-2-methyl-4-(2,6,6-trimethyl-1-cyclohexen-1-yl)-1,3-butadiene.
(E)-1-(2-carbopentoxy-5-pyrimidinyl)-2-methyl-4-(2,6,6-trimethyl-1-cyclohexen-1-yl)-1,3-butadiene.
(E)-1-(2-carbohexoxy-5-pyrimidinyl)-2-methyl-4-(2,6,6-trimethyl-1-cyclohexen-1-yl)-1,3-butadiene.
(E)-1-(2-carboheptoxy-5-pyrimidinyl)-2-methyl-4-(2,6,6-trimethyl-1-cyclohexen-1-yl)-1,3-butadiene.
(E)-1-(2-carboctoxy-5-pyrimidinyl)-2-methyl-4-(2,6,6-trimethyl-1-cyclohexen-1-yl)-1,3-butadiene.
(E)-1-(2-carbononoxy-5-pyrimidinyl)-2-methyl-4-(2,6,6-trimethyl-1-cyclohexen-1-yl)-1,3-butadiene.
(E)-1-(2-carbodecoxy-5-pyrimidinyl)-2-methyl-4-(2,6,6-trimethyl-1-cyclohexen-1-yl)-1,3-butadiene.
(E)-1-[2-carbo-(2-hydroxy)ethoxy-5-pyrimidinyl]-2-methyl-4-(2,6,6-trimethyl-1-cyclohexen-1-yl)-1,3-butadiene.
(E)-1-[2-carbo-(3-hydroxy)propoxy-5-pyrimidinyl]-2-methyl-4-(2,6,6-trimethyl-1-cyclohexen-1-yl)-1,3-butadiene.
(E)-1-(2-carbophenoxy-5-pyrimidinyl)-2-methyl-4-(2,6,6-trimethyl-1-cyclohexen-1-yl)-1,3-butadiene.
(E)-1-(2-carbo-p-hydroxyphenoxy-5-pyrimidinyl)-2-methyl-4-(2,6,6-trimethyl-1-cyclohexen-1-yl)-1,3-butadiene.
(E)-1-(2-carbo-p-hydroxyphenoxy-5-pyrimidinyl)-2-methyl-4-(2,6,6-trimethyl-1-cyclohexen-1-yl)-1,3-butadiene.
(E)-1-(2-carbo-o-hydroxyphenoxy-5-pyrimidinyl)-2-methyl-4-(2,6,6-trimethyl-1-cyclohexen-1-yl)-1,3-butadiene.
(E)-1-(2-carbo-p-methoxyphenoxy-5-pyrimidinyl)-2-methyl-4-(2,6,6-trimethyl-1-cyclohexen-1-yl)-1,3-butadiene.
(E)-1-(2-carbo-p-isopropoxyphenoxy-5-pyrimidinyl)-2-methyl-4-(2,6,6-trimethyl-1-cyclohexen-1-yl)-1,3-butadiene.
(E)-1-(2-carbo-2-toluoxy-5-pyrimidinyl)-2-methyl-4-(2,6,6-trimethyl-1-cyclohexen-1-yl)-1,3-butadiene.
(E)-1-(2-carbo-2-naphthoxy-5-pyrimidinyl)-2-methyl-4-(2,6,6-trimethyl-1-cyclohexen-1-yl)-1,3-butadiene.

Examples of carboxamide groups (R=NR$^1$R$^2$) represented by formula (1) are:

N-methyl (E)-5-[2-methyl-4-(2,6,6-trimethyl-1-cyclohexen-1-yl)butadien-1,3-yl]pyridine-2-carboxamide.
N-isopropyl (E)-5-[2-methyl-4-(2,6,6-trimethyl-1-cyclohexen-1-yl)butadien-1,3-yl]pyridine-2-carboxamide.
N-hexyl (E)-5-[2-methyl-4-(2,6,6-trimethyl-1-cyclohexen-1-yl)butadien-1,3-yl]pyridine-2-carboxamide.
N-octyl (E)-5-[2-methyl-4-(2,6,6-trimethyl-1-cyclohexen-1-yl)butadien-1,3-yl]pyridine-2-carboxamide.
N-hydroxymethyl (E)-5-[2-methyl-4-(2,6,6-trimethyl-1-cyclohexen-1-yl)butadien-1,3-yl]pyridine-2-carboxamide.
N-2-hydroxyethyl (E)-5-[2-methyl-4-(2,6,6-trimethyl-1-cyclohexen-1-yl)butadien-1,3-yl]pyridine-2-carboximide.
N-3-hydroxypropyl (E)-5-[2-methyl-4-(2,6,6-trimethyl-1-cyclohexen-1-yl)butadien-1,3-yl]pyridine-2-carboxamide.
N-3-hydroxypentyl (E)-5-[2-methyl-4-(2,6,6-trimethyl-1-cyclohexen-1-yl)butadien-1,3-yl]pyridine-2-carboxamide.
N,N-dimethyl (E)-5-[2-methyl-4-(2,6,6-trimethyl-1-cyclohexen-1-yl)butadien-1,3-yl]pyridine-2-carboxamide.
N-ethyl-N-methyl (E)-5-[2-methyl-4-(2,6,6-trimethyl-1-cyclohexen-1-yl)butadien-1,3-yl]pyridine-2-carboxamide.
N-methyl-N-octyl (E)-5-[2-methyl-4-(2,6,6-trimethyl-1-cyclohexen-1-yl)butadien-1,3-yl]pyridine-2-carboxamide.
N-phenyl (E)-5-[2-methyl-4-(2,6,6-trimethyl-1-cyclohexen-1-yl)butadien-1,3-yl]pyridine-2-carboxamide.
N-p-hydroxyphenyl (E)-5-[2-methyl-4-(2,6,6-trimethyl-1-cyclohexen-1-yl)butadien-1,3-yl]pyridine-2-carboxamide.
N-p-methoxyphenyl (E)-5-[2-methyl-4-(2,6,6-trimethyl-1-cyclohexen-1-yl)butadien-1,3-yl]pyridine-2-carboxamide.
N-p-butoxyphenyl (E)-5-[2-methyl-4-(2,6,6-trimethyl-1-cyclohexen-1-yl)butadien-1,3-yl]pyridine-2-carboxamide.
N-methyl (E)-4-[2-methyl-4-(2,6,6-trimethyl-1-cyclohexen-1-yl)butadien-1,3-yl]imidazole-2-carboxamide.
N-isopropyl (E)-4-[2-methyl-4-(2,6,6-trimethyl-1-cyclohexen-1-yl)butadien-1,3-yl]imidazole-2-carboxamide.
N-hexyl (E)-4-[2-methyl-4-(2,6,6-trimethyl-1-cyclohexen-1-yl)butadien-1,3-yl]imidazole-2-carboxamide.
N-octyl (E)-4-[2-methyl-4-(2,6,6-trimethyl-1-cyclohexen-1-yl)butadien-1,3-yl]imidazole-2-carboxamide.
N-hydroxymethyl (E)-4-[2-methyl-4-(2,6,6-trimethyl-1-cyclohexen-1-yl)butadien-1,3-yl]imidazole-2-carboxamide.
N-2-hydroxyethyl (E)-4-[2-methyl-4-(2,6,6-trimethyl-1-cyclohexen-1-yl)butadien-1,3-yl]imidazole-2-carboxamide.
N-3-hydroxypropyl (E)-4-[2-methyl-4-(2,6,6-trimethyl-1-cyclohexen-1-yl)butadien-1,3-yl]imidazole-2-carboxamide.
N-3-hydroxypentyl (E)-4-[2-methyl-4-(2,6,6-trimethyl-1-cyclohexen-1-yl)butadien-1,3-yl]imidazole-2-carboxamide.
N,N-dimethyl (E)-4-[2-methyl-4-(2,6,6-trimethyl-1-cyclohexen-1-yl)butadien-1,3-yl]imidazole-2-carboxamide.
N-ethyl-N-methyl (E)-4-[2-methyl-4-(2,6,6-trimethyl-1-cyclohexen-1-yl)butadien-1,3-yl]imidazole-2-carboxamide.
N-methyl-N-octyl (E)-4-[2-methyl-4-(2,6,6-trimethyl-1-cyclohexen-1-yl)butadien-1,3-yl]imidazole-2-carboxamide.
N-phenyl (E)-4-[2-methyl-4-(2,6,6-trimethyl-1-cyclohexen-1-yl)butadien-1,3-yl]imidazole-2-carboxamide.

N-p-hydroxyphenyl (E)-4-[2-methyl-4-(2,6,6-trimethyl-1-cyclohexen-1-yl)butadien-1,3-yl]imidazole-2-carboxamide.

N-p-methoxyphenyl (E)-4-[2-methyl-4-(2,6,6-trimethyl-1-cyclohexen-1-yl)butadien-1,3-yl]imidazole-2-carboxamide.

N-p-butoxyphenyl (E)-4-[2-methyl-4-(2,6,6-trimethyl-1-cyclohexen-1-yl)butadien-1,3-yl]imidazole-2-carboxamide.

N-methyl (E)-5-[2-methyl-4-(2,6,6-trimethyl-1-cyclohexen-1-yl)butadien-1,3-yl]pyrazine-2-carboxamide.

N-isopropyl (E)-5-[2-methyl-4-(2,6,6-trimethyl-1-cyclohexen-1-yl)butadien-1,3-yl]pyrazine-2-carboxamide.

N-hexyl (E)-5-[2-methyl-4-(2,6,6-trimethyl-1-cyclohexen-1-yl)butadien-1,3-yl]pyrazine-2-carboxamide.

N-octyl (E)-5-[2-methyl-4-(2,6,6-trimethyl-1-cyclohexen-1-yl)butadien-1,3-yl]pyrazine-2-carboxamide.

N-hydroxymethyl (E)-5-[2-methyl-4-(2,6,6-trimethyl-1-cyclohexen-1-yl)butadien-1,3-yl]pyrazine-2-carboxamide.

N-2-hydroxyethyl (E)-5-[2-methyl-4-(2,6,6-trimethyl-1-cyclohexen-1-yl)butadien-1,3-yl]pyrazine-2-carboxamide.

N-3-hydroxypropyl (E)-5-[2-methyl-4-(2,6,6-trimethyl-1-cyclohexen-1-yl)butadien-1,3-yl]pyrazine-2-carboxamide.

N-3-hydroxypentyl (E)-5-[2-methyl-4-(2,6,6-trimethyl-1-cyclohexen-1-yl)butadien-1,3-yl]pyrazine-2-carboxamide.

N,N-dimethyl (E)-5-[2-methyl-4-(2,6,6-trimethyl-1-cyclohexen-1-yl)butadien-1,3-yl]pyrazine-2-carboxamide.

N-ethyl-N-methyl (E)-5-[2-methyl-4-(2,6,6-trimethyl-1-cyclohexen-1-yl)butadien-1,3-yl]pyrazine-2-carboxamide.

N-methyl-N-octyl (E)-5-[2-methyl-4-(2,6,6-trimethyl-1-cyclohexen-1-yl)butadien-1,3-yl]pyrazine-2-carboxamide.

N-phenyl (E)-5-[2-methyl-4-(2,6,6-trimethyl-1-cyclohexen-1-yl)butadien-1,3-yl]pyrazine-2-carboxamide.

N p-hydroxyphenyl (E)-5-[2-methyl-4-(2,6,6-trimethyl-1-cyclohexen-1-yl)butadien-1,3-yl]pyrazine-2-carboxamide.

N-p-methoxyphenyl (E)-5-[2-methyl-4-(2,6,6-trimethyl-1-cyclohexen-1-yl)butadien-1,3-yl]pyrazine-2-carboxamide.

N-p-butoxyphenyl (E)-5-[2-methyl-4-(2,6,6-trimethyl-1-cyclohexen-1-yl)butadien-1,3-yl]pyrazine-2-carboxamide.

N-methyl (E)-5-[2-methyl-4-(2,6,6-trimethyl-1-cyclohexen-1-yl)butadien-1,3-yl]pyrimidine-2-carboxamide.

N-isopropyl (E)-5-[2-methyl-4-(2,6,6-trimethyl-1-cyclohexen-1-yl)butadien-1,3-yl]pyrimidine-2-carboxamide.

N-hexyl (E)-5-[2-methyl-4-(2,6,6-trimethyl-1-cyclohexen-1-yl)butadien-1,3-yl]pyrimidine-2-carboxamide.

N-octyl (E)-5-[2-methyl-4-(2,6,6-trimethyl-1-cyclohexen-1-yl)butadien-1,3-yl]pyrimidine-2-carboxamide.

N-hydroxymethyl (E)-5-[2-methyl-4-(2,6,6-trimethyl-1-cyclohexen-1-yl)butadien-1,3-yl]pyrimidine-2-carboxamide.

N-2-hydroxyethyl (E)-5-[2-methyl-4-(2,6,6-trimethyl-1-cyclohexen-1-yl)butadien-1,3-yl]pyrimidine-2-carboxamide.

N-3-hydroxypropyl (E)-5-[2-methyl-4-(2,6,6-trimethyl-1-cyclohexen-1-yl)butadien-1,3-yl]pyrimidine-2-carboxamide.

N-3-hydroxypentyl (E)-5-[2-methyl-4-(2,6,6-trimethyl-1-cyclohexen-1-yl)butadien-1,3-yl]pyrimidine-2-carboxamide.

N,N-dimethyl (E)-5-[2-methyl-4-(2,6,6-trimethyl-1-cyclohexen-1-yl)butadien-1,3-yl]pyrimidine-2-carboxamide.

N-ethyl-N-methyl (E)-5-[2-methyl-4-(2,6,6-trimethyl-1-cyclohexen-1-yl)butadien-1,3-yl]pyrimidine-2-carboxamide.

N-methyl-N-octyl (E)-5-[2-methyl-4-(2,6,6-trimethyl-1-cyclohexen-1-yl)butadien-1,3-yl]pyrimidine-2-carboxamide.

N-phenyl (E)-5-[2-methyl-4-(2,6,6-trimethyl-1-cyclohexen-1-yl)butadien-1,3-yl]pyrimidine-2-carboxamide.

N-p-hydroxyphenyl (E)-5-[2-methyl-4-(2,6,6-trimethyl-1-cyclohexen-1-yl)butadien-1,3-yl]pyrimidine-2-carboxamide.

N-p-methoxyphenyl (E)-5-[2-methyl-4-(2,6,6-trimethyl-1-cyclohexen-1-yl)butadien-1,3-yl]pyrimidine-2-carboxamide.

N-p-butoxyphenyl (E)-5-[2-methyl-4-(2,6,6-trimethyl-1-cyclohexen-1-yl)butadien-1,3-yl]pyrimidine-2-carboxamide.

The retinoids of formula (1) where X is a carbonyl pyridine and R is ethoxy may be made in a stereospecific manner by the following route (Et=ethyl):

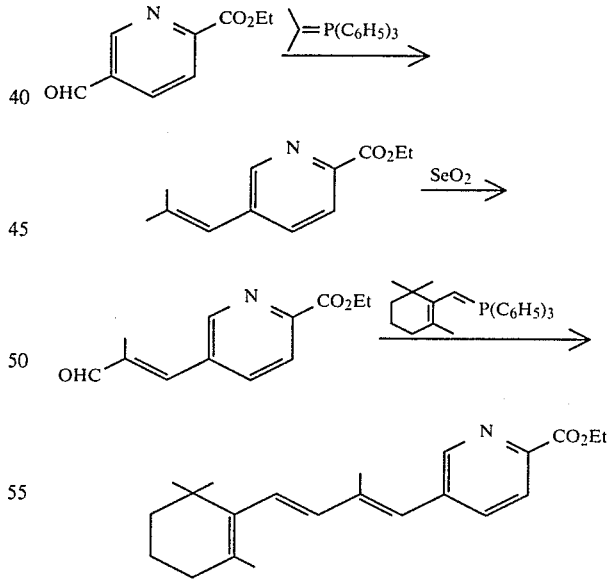

Other esters and esters of the other heterocycles of formula (1) may be made by starting with the desired ester aldehyde of the appropriate heterocycles.

Likewise amides are synthesised by using the appropriate amide aldehyde as the starting material.

The acids are generally prepared by alkaline hydrolysis of the ethyl esters as given in the following scheme:

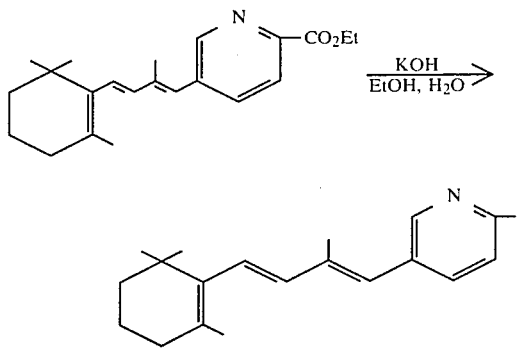

The amides may then also be made from the acids by conversion to acid chlorides or activated ester followed by reaction with an appropriate amine.

The following example is provided to further illustrate the compounds and their preparation. It is not intended to limit the invention in any manner. Abbreviations used in the following example are: Me=methyl; Et=ethyl; Pr=propyl; Bu=butyl; THF=tetrahydrofuran; LC=high-performance liquid chromatography; IR=infrared; NMR=nuclear magnetic resonance; UV=ultraviolet; DMF=dimethylformamide; GC=gas chromatography; TLC=thin layer chromatography; and mp=melting point.

EXAMPLE

Preparation of (E)-1-(2-Carbethoxy-5-pyridyl)-2-methyl-4-(2,6,6-trimethyl-1-cyclohexen-1-yl)-1,3-butadiene Diethyl Pyridine-2,5-dicarboxylate. To a suspension of 100 g (0.6 mol) of 2,5-pyridinedicarboxylic acid in 300 mL of absolute EtOH was added 100 mL of concentrated $H_2SO_4$ over a period of 1.5 h. During this time, the solid gradually all went into solution. The brown reaction mixture was refluxed for 16 h. Then 200 mL of benzene was added and the benzene/EtOH/$H_2O$ azeotrope was removed at the rate of 30 mL/30 min, with more 1:1 benzene/EtOH mixture added at 30-min intervals. After 5 h, the reaction mixture was poured onto 30 L of ice-water. Solid $NaHCO_3$ was then added until the mixture was neutralized. The product was extracted into EtOAc. The EtOAc layer was washed with brine, dried ($Na_2SO_4$), and concentrated to 99.8 g of a yellow solid, which was purified on 400 g of silica gel (25% $Et_2O$/hexane and 50% $Et_2O$/hexane) to give 95 g of solid. Recrystallization from $Et_2O$/hexane gave 90 g of the diethyl ester, diethyl pyridine-2,5-dicarboxylate, as pale yellow crystals, mp 46°–47° C.; IR (mull) 1730, 1710, 1600, 1375, 1280, 1250, 1100, 1030, 750 cm$^{-1}$; $^1$H NMR (CDCl$_3$) $\delta$1.47 and 1.50 (2 t, J=7.5 Hz, 6, CO$_2$CH$_2$CH$_3$), 4.55 and 4.62 (2 q, J=7.5 Hz, 4, CO$_2$CH$_2$CH$_3$), 8.17 (d, J=8 Hz, 1, 3'—H), 8.47 (dd, J=2.5 Hz, J=8 Hz, 1, 4'—H), 9.33 d, J=2.5 Hz, 1,6'—H).

2-Formyl-5-hydroxymethylpyridine. To a solution of 33.5 g (0.15 mol) of diethyl pyridine-2,5-dicarboxylate in 300 mL of absolute EtOH was added 11.4 g (0.3 mol) of NaBH$_4$ in several portions over a 30-min period. Then a solution of 33.3 g (0.3 mol) of anhydrous CaCl$_2$ in 200 ml of EtOH was added dropwise over a 1-h period. The mixture was stirred at room temperature for 16 h, and then it was neutralized with 12 to 13 mL of concentrated $H_2SO_4$. The CaSO$_4$, which precipitated, was removed by centrifugation (two EtOH washings). The combined supernatant was concentrated, dissolved in about 10 mL of $H_2O$, and applied to a 4.5×18-cm column of Dowex 50W-X8 cation exchange resin (H+ form). The column was eluted with $H_2O$ until the eluate was no longer acidic, and then it was eluted with dilute NH$_4$OH, which removed the 2,5-pyridinedimethanol from the column. Evaporation afforded 10.6 g (51% yield) of 2,5-pyridinedimethanol as a light brown hygroscopic solid: $^1$H NMR (Me$_2$SO-d$_6$) $\delta$4.55 and 4.59 (2 s, 4, CH$_2$OH), 5.23 (broad s, 2, CH$_2$OH), 7.42 (d, J=8 Hz, 1, 3'—H), 7.72 (dd, J=2 Hz, J=8 Hz, 1, 4—H), 8.42 (d, J=2 Hz, 1, 6'—H).

The crude product, 2,5-pyridinedimethanol, (10.5 g, 0.076 mol) was dissolved in 80 mL of dioxane and 2 mL of $H_2O$ and 4.0 g (0.039 mol) of SeO$_2$ was added. The mixture was degassed three times under argon and then heated at 100° C. for 3 h. The cooled reaction mixture was filtered through Celite (30-mL dioxane wash). The filtrate and washings were concentrated to about 10 mL volume and chromatographed on 150 g of silica gel (50% EtOAc/hexane and 75% EtOAc/hexane) to give 6.2 g (59% yield) of the aldehyde, 2-formyl-5-hydroxymethylpyridine, as a pale yellow solid. A portion was recrystallized from EtOAc/hexane to give white plates, mp 75° C.; IR (mull) 3250, 1700, 1600, 1580, 1460, 1230, 1190, 1060, 1030, 830, 770 cm$^{-1}$; $^1$H NMR (CDCl$_3$) $\delta$4.23 (broad s, 1, OH), 4.90 (s, 2, CH$_2$), 7.95 and 7.97, (2 m, 2, 3', 4'—H), 8.77 (m, 1, 6'—H); MS calcd for C$_7$H$_7$NO$_2$ 137.0478, found 137.0471.

2-Carbethoxy-5-hydroxymethylpyridine. 2-Formyl-5-hydroxymethylpyridine (5.7 g, 0.042 mol) was dissolved in 40 mL of $H_2O$ and treated with 10 mL of aqueous 30% $H_2O_2$ at room temperature for 16 h. The mixture was concentrated to about 20 mL and cooled, and the precipitated acid was collected by filtration. 2-Carboxy-5-hydroxymethylpyridine was obtained in 97% yield (6.1 g). A portion was recrystallized from $H_2O$ to obtain an analytical sample. These white crystals sublimed at about 220° C., IR (mull) 3200, 1670, 1600, 1380, 1070, 870, 850, 800 cm$^{-1}$; $^1$H NMR (Me$_2$SO-d$_6$) $\delta$4.73 (s, 2, CH$_2$OH), 7.9–8.2 (m, 2, 3', 4'—H), 8.67 (m, 1, 6'—H); MS calcd for C$_7$H$_7$NO$_3$ 153.0426, found 153.0429.

To a solution of 10 g (0.065 mol) of the acid in 80 mL of EtOH and 10 mL of Et$_3$N was added a solution of 3.65 g (0.033 mol) of CaCl$_2$ in 25 mL of EtOH. The mixture was evaporated to dryness under vacuum and then was refluxed for 4 h with a mixture of 80 mL of EtOH and 25 mL of $H_2SO_4$. The combined filtrate and washings were concentrated to about a 40-mL volume, which was diluted with 100 mL of ice-water. The mixture was neutralized with solid NaHCO$_3$ and extracted with CHCl$_3$ (6×70 mL). The organic extract was dried (Na$_2$SO$_4$) and concentrated to give 11.0 g of the ester as a light yellow solid (93% yield), mp 64° C., IR (mull) 3300, 1725, 1595, 1590, 1480, 1390, 1310, 1290, 1150, 1070, 1030, 860, 780, 705 cm$^{-1}$; $^1$H NMR (CDCl$_3$) $\delta$1.42 (t, J=7 Hz, 3, CH$_3$), 4.43 (q, J=7 Hz, 2, CH$_2$CH$_3$), 4.82 (s, 2, CH$_2$OH), 4.95 (broad s, 1, OH), 7.82 (dd, J=2 Hz, J=8 Hz, 1, 4'—H), 8.03 (d, J=8 Hz, 1, 3'—H), 8.67 (d, J=2 Hz, 1, 6'—H); MS calcd for C$_9$H$_{11}$NO$_3$ 181.0739, found 181.0739.

2-Carbethoxy-5-formylpyridine. To a stirred solution of 30 mL (0.37 mol) of pyridine in 150 mL of CH$_2$Cl$_2$ at 0° C. was added 18.0 g (0.18 mol) of CrO$_3$ over a period of 30 min. The orange mixture was stirred at 0° C. for another 20 min before a solution of 11.0 (0.061 mol) of the alcohol 2-carbethoxy-5-hydroxymethylpyridine in 20 mL of CH$_2$Cl$_2$ was added. The mixture was stirred at room temperature for 4 h and filtered through florisil. The filtrate was concentrated and purified on 150 g of silica gel (1 L of 50% EtOAc/hexane followed by 75% EtOAc/hexane) to give 6.4 g (59% yield) of the product 2-carbethoxy-5-formylpyridine as white crystals, mp 59° C.; IR (melt) 1720, 1600, 1570, 1370, 1310, 1250, 1120, 1020, 835, 795, 700 cm$^{-1}$; $^1$H NMR (CDCl$_3$) δ1.48 (t, J=7 Hz, 3, CH$_3$), 4.52 (q, J=7 Hz, 2, CH$_2$), 8.33 (broad m, 2, 3', 4'—H), 9.20 (broad m, 1, 6'—H), 10.27 (s, 1, CHO); MS calcd for C$_9$H$_9$NO$_3$, 179.0582, found 179.0572.

1-(2-Carbethoxy-5-pyridyl)-2-methyl-1-propene. A suspension of 15.21 g (35.0 mmol) of isopropyltriphenylphosphonium iodide in 200 mL of THF was cooled to −20° C. and 23.4 mL (35 mmol) of a 1.5M solution of n-BuLi in hexane was added over a 10-min period. The mixture was gradually warmed to 0° C. over a period of 30 min before 6.3 g (35.2 mmol) of the aldehyde 2-carbethoxy-5-formylpyridine in 15 mL of THF was added. The reaction mixture was stirred at room temperature for 16 h and at 55°-60° C. for 1 h. The cooled reaction mixture was filtered through Celite. The filtrate was concentrated and filtered again and chromatographed on 150 g of silica gel (50% EtOAc/hexane and 75% EtOAc/hexane) to give 4.7 g of the product, 1-(2-carbethoxy-5-pyridyl)-2-methyl-1-propene, as a yellow oil (65% yield): IR (film) 3000, 2950, 1730, 1670, 1600, 1580, 1470, 1410, 1390, 1330, 1280, 1230, 1190, 1150, 1120, 1040, 890, 800, 730 cm$^{-1}$; $^1$H NMR (CDCl$_3$) δ1.45 (t, J=Hz, 3, CO$_2$CH$_2$CH$_3$), 1.92 and 1.99 (2 s, 6, C=C(CH$_3$)$_2$), 4.50 (q, J=Hz, 2, CO$_2$CH$_2$CH$_3$), 6.30 (s, 1, C=CH), 7.67 (dd, J=2 Hz, J=8 Hz, 1, 4'—H), 8.13 (d, J=8 Hz, 1, 3'—H), 8.67 (d, J=2 Hz, 1, 6'—H); MS calcd for C$_{12}$H$_{15}$NO$_2$ 205.1103, found 205.1118.

3-(2-Carbethoxy-5-pyridyl)-2-methyl-2-propenal. A mixture of 5.0 g (45.0 mmol) of SeO$_2$ and 4.25 g (20.7 mmol) of 1-(2-carbethoxy-5-pyridyl)-2-methyl-1-propene in 50 mL of dioxane and 2 mL of H$_2$O was degassed three times under argon and then heated at 100° C. for 2 h. The mixture was filtered through Celite and washed with dioxane. The filtrate was concentrated and chromatographed on 150 g of silica gel (50% EtOAc/hexane and 75% EtOAc/hexane) to give 2.95 g of 3-(2-carbethoxy-5-pyridyl)-2-methyl-2-propenal as a yellow solid. Analytical LC (Radialpak B, 25% EtOAc/hexane) indicated about 5% of the Z isomer was present. Recrystallization from EtOAc/hexane gave 2.4 g (53% yield) of the pure E isomer as white crystals, mp 72°-73° C.; IR (mull) 1740, 1700, 1330, 1300, 1260, 1200, 1170, 1140, 1120, 1020, 920, 880, 830, 810, 720 cm$^{-1}$; $^1$H NMR (CDCl$_3$) δ1.50 (t, J=7 Hz, 3, CO$_2$CH$_2$CH$_3$), 2.10 (s, 3, C=CCH$_3$), 4.50 (q, J=7 Hz, 2, CO$_2$CH$_2$CH$_3$), 7.35 (s, 1, C=CH), 8.02 (dd, J=2 Hz, J=8 Hz, 1, 4'—H), 8.27 (d, J=8 Hz, 1, 3'—H), 8.93 (d, J=1 Hz, 1, 6'—H), 9.70 (s, 1, CHO); MS calcd for C$_{12}$H$_{13}$NO$_3$ 219.0895, found 219.0907.

(E)-1-(2-Carbethoxy-5-pyridyl)-2-methyl-4-(2,6,6-trimethyl-1-cyclohexen-1-yl)-1,3-butadiene. To a suspension of 5.25 g (11.0 mmol) of β-cyclogeranyltriphenylphosphonium bromide in 150 mL of THF at −20° C. was added 7.2 mL of a 1.54M solution of n-BuLi (11.0 mmol) in hexane. The dark brown mixture was stirred at 0° C. for 30 min. Then 2.40 g (10.95 mmol) of 3-(2-carbethoxy-5-pyridyl)-2-methyl-2-propenal in 10 mL of THF was added. The mixture was stirred overnight at room temperature and at 50°-60° C. for 1 h. The resulting yellow solution was concentrated to about 20 mL, diluted with 50 mL EtOAc, and filtered through Celite. The filtrate was washed with 100 mL of brine, dried (Na$_2$SO$_4$), and concentrated to afford about 6.0 g of a yellow oil. The oil was purified on 120 g of silica gel (25% EtOAc/hexane) to give 2.8 g (75% yield) of a bright yellow oil, which was further purified by preparative LC (10% Et$_2$O/hexane containing 0.3% i-PrOH to give 2.2 g of the product as a light yellow oil: LC (Radialpak B, 10% EtOAc and 0.5% i-PrOH in hexane, 2 mL/min, 260 nm) t$_R$ 4.0 (97.5%), 4.6 min (2.5%); LC (Radialpak A, 10% H$_2$O/CH$_3$CN, 2 mL/min, 260 nm) t$_R$ 6.42 (97%), 7.47 min (3%); Ir (film) 2950, 1720, 1620, 1600, 1570, 1470, 1380, 1320, 1260, 1200, 1150, 1130, 1040, 980, 950, 890, 800, 720 cm$^{-1}$; $^1$H NMR (CDCl$_3$) δ1.07 (s, 6, 16$_R$, 17$_R$ CH$_3$), 1.45 (t, J=7 Hz, 3, CH$_2$CH$_3$), 1.4-1.7 (m, 4, 2$_R$, 3$_R$ CH$_2$), 1.75 (s, 3, 18$_R$ CH$_3$), 1.8-2.1 (m, 2, 4$_R$ CH$_2$), 2.15 (s, 3, 19$_R$ CH$_3$), 4.50 (q, J=7 Hz, 2, CH$_2$CH$_3$), 6.32 (m, 2, 7$_R$, 8$_R$ HC=CH), 6.48 (s, 10$_R$ C=$\overline{\text{CH}}$), 7.77 (dd, J=2 Hz, J=8 Hz, 1, 4'—H), 8.15 (d, J=8 Hz, 1, 3'—H), 8.72 (d, J=2 Hz, 1, 6'—H); $^{13}$C NMR (CDCl$_3$) 13.8, 14.2 (19$_R$, OCH$_2$CH$_3$), 19.0 (3$_R$), 21.5 (18$_R$), 28.7 (16$_R$, 17$_R$), 32.8 (4$_R$), 34.0 (1$_R$), 39.3 (2$_R$), 61.5 (OCH$_2$), 124.3, 124.7 (10$_R$, 3', 5'), 129.2, 129.7 (5$_R$, 7$_R$), 136.1, 137.0, 137.2 (6$_R$, 8$_R$, 4'), 140.2 (9$_R$), 145.0 (6'), 150.0 (2'), 164.9 ppm (C=O); UV (EtOH) λ$_{max}$ 334 nm (ε2.22×10$^4$), 266 nm (ε1.2×10$^4$); MS calculated for C$_{22}$H$_{29}$NO$_2$ 339.2198, found 339.2206.

The retinoids of formula (1) may be used topically or systemically as chemopreventive agents and in the treatment, amelioration, or prevention of the skin disorders and rheumatic disorders for which retinoic acid and other retinoids are useful. In this regard, they may be used for therapy in animals, including humans, of premalignant epithelial cell lesions, as a prophylaxis against tumor promotion in epithelial cells and treatment for dermatoses such as icthyoses, follicular disorders, benign epithelial disorders, and other proliferative skin diseases (nonmalignant conditions of the skin that are characterized by epidermal cell proliferation or incomplete cell differentiation) such as acne, psoriasis, eczema, atopic dermatitis, nonspecific dermatitis and the like. When used for such treatments they will usually be formulated with a pharmaceutical liquid, semisolid, or solid carrier. A pharmaceutically acceptable carrier is a material that is nontoxic and generally inert and does not affect the functionality of the active ingredients adversely. Such materials are well known and include those materials sometimes referred to as diluents or vehicles in the pharmaceutical formulation art. The carrier may be organic or inorganic in nature. Examples of pharmaceutically acceptable carriers that may be used to formulate the retinoids are water, gelatin, lactose, starch, mineral oil, cocoa butter, dextrose, sucrose, sorbitol, mannitol, gum acacia, alginates, cellulose, talc, magnesium stearate, polyoxyethylene sorbitan monolaurate, and other commonly used pharmaceutical carriers. In addition to the retinoid and carrier the formulation may contain minor amounts of additives such as flavoring agents, coloring agents, thickening or gelling agents, emulsifiers, wetting agents, buffers, stabilizers, and preservatives such as antioxidants.

For topical administration the retinoids are conveniently provided in the form of ointments, tinctures, creams, solutions, lotions, sprays, suspensions, and the like. The amount of retinoid in such topical formulations will normally be in the range of about 0.01 to about 1% by weight. For enteral (oral or rectal) administration the retinoids will typically be formulated as tablets, capsules, dragees, syrups, solutions, or suppositories. For parenteral administration the retinoids will be formulated as injectable solutions or suspensions.

The dosages and dosage regimen in which the retinoids are administered will vary according to, the dosage form, mode of administration, the condition being treated and particulars of the patient being treated. They will, of course, be administered in chemopreventive (tumor promotion inhibiting) amounts or therapeutically effective amounts. For adult humans such chemopreventive amounts will usually be about 0.01 mg to 10.0 mg daily given in one or more doses. Oral doses will generally be less than topical doses and doses for treating skin disorders will typically be less than doses administered for cancer chemoprevention. The dose for treating skin disorders will be on the order of, but normally less than, the dose of retinoic acid prescribed for the disorder.

The usefulness of the invention compounds was demonstrated by testing the compound of the Example in the ornithine decarboxylase (ODC) assay, Verma, A. K. and Boutwell, R. K., *Cancer Res* (1977) 37:2196–2201; and the tracheal organ culture assay, Newton, D. L.; Henderson, W. R.; and Sporn, M. B., *Cancer Res* (1980) 40:3413–3425. The ODC assay measures a compound's ability to prevent the induction of ODC. The tracheal organ culture assay measures a compound's ability to reverse keratinization.

The ODC assay is carried out as follows. Female Charles River CD-1 mice from Charles River Breeding Laboratories, Wilmington, Mass., are used (age 7 to 9 weeks). The dorsal hair of the mice is shaved 1 to 2 days before testing, and only mice showing no hair regrowth are used. A single dose of 12-O-tetradecanoylphorbol-13-acetate (TPA) (10.5 $\mu$g, 17 nmol) in 0.2 mL of acetone is applied topically to the back of each mouse. The test compound, at one of three dose levels (1.7, 17 and 170 nmol), dissolved in 0.2 mL of acetone is applied 1 hour before the TPA treatment to the test groups; the control group is treated with acetone alone. The mice are killed by cervical dislocation five hours after TPA treatment. Determinations are done in triplicate.

The epidermis is obtained from the sacrificed animals. To obtain sufficient material, the dorsal skins from 2 to 3 mice in each treatment group are pooled. The depilatory agent Nudit ® (Helena Rubinstein, New York) is applied to the shaved area of the skin; after 5 minutes, it is washed off thoroughly with cold tap water. Then the skin is excised and plunged immediately into ice-cold water; it is then placed in a 55° C. water bath for 30 seconds and reimmersed in ice-cold water for at least another 30 seconds. The skin is placed epidermis side up on a cold plate, and the epidermis is scraped off with a razor blade. The pooled epidermal sheets are homogenized (Polytron PT-10 homogenizer) at 0° to 4° C. for 15–20 seconds in 50 mM sodium phosphate and 0.1 mM ethylenediaminetetraacetic acid (EDTA), at a volume of 1 mL/skin.

The supernatant fraction remaining after centrifugation of the homogenate at 10,000$\times$g for 30 seconds at 0° C. is used for the enzyme assay. Enzyme activity is determined using the microassay for ODC as described by Verma and Boutwell to measure the release of $^{14}CO_2$ from DL-[1-$^{14}$C]-ornithine (58 mCi/mmol) after incubation with the 10,000$\times$g supernatant. The incubations are carried out by decanting, with a Pasteur pipette, 100 $\mu$L of the supernatant containing 100 to 120 $\mu$g of protein into two or three 15-mL Corex tubes in a shaking water bath at 37° C. The assay mixture in the tubes consists of 50 $\mu$L of 100 mM sodium phosphate buffer (pH 7.2), 10 $\mu$L of 4 mM pyridoxal phosphate, 40 $\mu$L of 25 mM dithiothreitol, and 1 $\mu$L of 0.1M EDTA. The center wells in the tubes are filled with 200 $\mu$L of a 2:1 solution (v/v) of ethanolamine:2-methoxyethanol. The reaction is started by adding 50 $\mu$L of substrate (0.5 $\mu$Ci of DL-[1-$^{14}$C]-ornithine in 2 mM cold ornithine) at 1-minute intervals by injection to each of the stoppered tubes. Incubations are routinely carried out at 37° C. for 30 to 60 minutes. The reaction is stopped by addition of 0.5 ml of 2M citric acid, and incubation is continued for an additional hour without heating to ensure complete absorption of $^{14}CO_2$.

Radioactivity is measured using a toluene-based scintillant (4 g of PPO and 50 mg of POPOP/L of toluene) in a Beckman LS-250 liquid scintillation counter. Enzyme activity is determined in triplicate and expressed as nanomoles of $CO_2$ released in 30 minutes per milligram of protein. Enzyme activity is linear for the protein concentration used. The protein concentrations of the epidermal extracts are determined by the Lowry procedure, using bovine serum albumin as the standard.

The tracheal organ culture assay is carried out as follows. Tracheas are taken from hamsters that are in very early stages of vitamin A deficiency and placed in organ culture. At the time of culture, the animals are still gaining weight; the tracheal epithelium is generally low columnar or cuboidal, with only occasional patches of squamous metaplasia. Each trachea is opened from the larynx to the carina along the membranous dorsal wall and cultured in a serum-free medium (CMRL-1066; with crystalline bovine insulin, 0.1 $\mu$g/ml; hydrocortisone hemisuccinate, 0.1 $\mu$g/ml; glutamine, 2 mM; penicillin, 100 units/ml; and streptomycin, 100 $\mu$g/ml, added). Cultures are gassed with 50% oxygen, 45% nitrogen, and 5% $CO_2$. The culture dishes are rocked at 35.5–36.0 degrees to allow the tracheas contact with both gas and medium. All tracheas are grown in medium containing no retinoid for the first 3 days. At the end of 3 days, some tracheas are harvested; almost of these tracheas have significant squamous metaplasia, and approximately 60% have keratinized lesions. The remaining tracheas are then divided into different groups which are treated with either: (1) retinoid dissolved in dimethylsulfoxide (final concentration of DMSO in culture medium is never greater than 0.1%) or (2) an equivalent amount of DMSO alone. Culture medium is changed three times a week, and all of the remaining tracheas are harvested at the end of 10 days in culture. Tracheas are fixed in 10% buffered formalin and embedded in paraffin. Cross sections of five micrometers are made through the mid-portion, stained with hematoxylin and eosin, and then scored with a microscope for the presence of keratin and keratohyaline granules, both of which are found in approximately 90% of control cultures that received no retinoid for the entire 10 day culture period. Retinoids are scored as "inactive" of both keratin and keratohyaline granules are seen; they are scored as "active" if neither keratin nor keratohyaline granules are seen, or if keratohyaline granules alone are absent.

The table below gives the results of these tests.

| | Reversal of Keratinization in Hamster Tracheal Organ Culture | | Inhibition of Induction of Ornithine Decarboxylase by 12-O—Tetradecanoyl-phorbol-13-acetate in Mouse Skin | |
|---|---|---|---|---|
| Test Compounds | Conc (M) | Active/Total Cultures (%) | Dose (nmol) | % Inhibition of Control |
| Retinoic Acid | $10^{-8}$ | 236/236 (100) | 17 | 87–91 |
| | $10^{-9}$ | 419/474 (88) | | |
| | $10^{-10}$ | 134/256 (52) | | |
| Example | $10^{-8}$ | 7/7 (100) | 17 | 68 |
| | $10^{-9}$ | 8/14 (57) | 1.7 | 29 |
| | $10^{-10}$ | 4/14 (29) | | |
| | $10^{-11}$ | 1/7 (14) | | |

These results indicate that the N-heterocyclic retinoic acid analogues of the invention possess biological activity that makes them useful as chemopreventive agents and therapeutic agents for treating nonmalignant skin disorders. Also because of the difference in structure and other chemical characteristics these N-heterocyclic retinoids may be less toxic than retinoic acid or its other aromatic analogues.

Modifications of the above described modes for carrying out the invention that are obvious to those of skill in the fields of organic chemistry, pharmaceuticals, and/or medicine are intended to be within the scope of the following claims.

What is claimed is:

1. A compound of the formula:

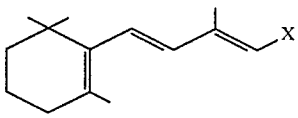

where X is

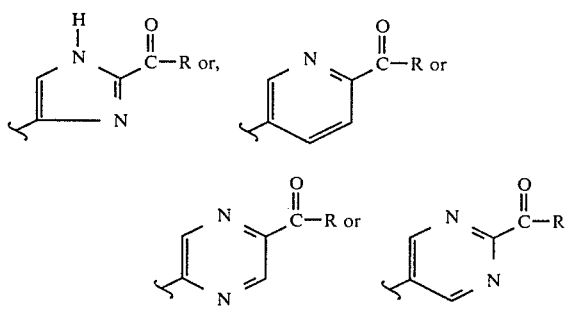

and R is hydroxy, alkoxy of 1 to 10 carbon atoms with 0 or 1 hydroxy substituent, phenoxy, monohydroxyphenoxy, monoalkoxyphenoxy where the alkoxy group contains 1 to 4 carbon atoms with 0 or 1 hydroxy substituent, or —NR$^1$R$^2$ where R$^1$ is hydrogen, alkyl of 1 to 8 carbon atoms with 0 or 1 hydroxy substituent, phenyl, 4-hydroxyphenyl, or 4-methoxyphenyl, and R$^2$ is alkyl of 1 to 8 carbon atoms with 0 or 1 hydroxy substituent, phenyl, 4-hydroxyphenyl, or 4-methoxyphenyl.

2. The compound of claim 1 wherein the alkoxy group represented by R contains 1 to 4 carbon atoms and the alkyl groups represented by R$^1$ and R$^2$ each contain 1 to 4 carbon atoms.

3. The compound of claim 1 wherein R is ethoxy or hydroxy.

4. A compound of the formula:

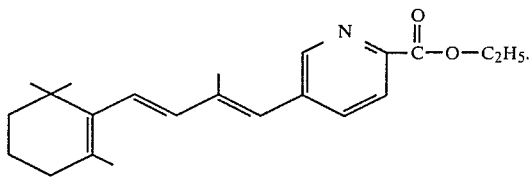

5. A therapeutic composition for treating a nonmalignant skin disorder susceptible to treatment by retinoic acid comprising a therapeutically effective amount of the compound of claim 1, combined with a pharmaceutically acceptable carrier.

6. A therapeutic composition for treating a nonmalignant skin disorder susceptible to treatment by retinoic acid comprising a therapeutically effective amount of the compound of claim 2, combined with a pharmaceutically acceptable carrier.

7. A therapeutic composition for treating a nonmalignant skin disorder susceptible to treatment by retinoic acid comprising a therapeutically effective amount of the compound of claim 3, combined with a pharmaceutically acceptable carrier.

8. A therapeutic composition for treating a nonmalignant skin disorder susceptible to treatment by retinoic acid comprising a therapeutically effective amount of the compound of claim 4, combined with a pharmaceutically acceptable carrier.

9. A method of treating a living animal for a nonmalignant skin disorder susceptible to treatment by retinoic acid comprising administering a therapeutically effective amount of the compound of claim 1 to the animal.

10. The method of claim 9 wherein the animal is a human.

11. A method of treating a living animal for a nonmalignant skin disorder susceptible to treatment by retinoic acid comprising administering a therapeutically effective amount of the compound of claim 2 to the animal.

12. The method of claim 11 where the animal is a human.

13. A method of treating a living animal for a nonmalignant skin disorder susceptible to treatment by retinoic acid comprising administering a therapeutically effective amount of the compound of claim 3 to the animal.

14. The method of claim 13 wherein the animal is a human.

15. A method of treating a living animal for a nonmalignant skin disorder susceptible to treatment by retinoic acid comprising administering a therapeutically effective amount of the compound of claim 4 to the animal.

16. The method of claim 15 where the animal is a human.

17. The therapeutic composition of claim 5 wherein the disorder is icthyoses, a follicular disorder, acne, psoriasis, eczema, atopic dermatitis, or nonspecific dermatitis.

18. The method of claim 9 wherein the disorder is icthyoses, a follicular disorder, acne, psoriasis, eczema, atopic dermatitis, or nonspecific dermatitis.

* * * * *